US00PP35508P2

(12) United States Plant Patent
Blom

(10) Patent No.: US PP35,508 P2
(45) Date of Patent: Nov. 28, 2023

(54) ***CHRYSANTHEMUM* PLANT NAMED 'ZANMUTRIBE YELLOW'**

(50) Latin Name: ***Chrysanthemum* X *morifolium***
Varietal Denomination: Zanmutribe Yellow

(71) Applicant: Wilhelmus Bernardus Blom, Leimuiden (NL)

(72) Inventor: Wilhelmus Bernardus Blom, Leimuiden (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 18/122,349

(22) Filed: Mar. 16, 2023

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289, 295
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Chrysanthemum* plant named 'Zanmutribe Yellow', characterized by its upright, outwardly spreading and uniformly spherical plant habit; moderately vigorous growth habit and moderate growth rate; freely branching habit; dense and full plant habit; early and freely flowering habit; long flowering period; decorative-type inflorescences with ray florets that are yellow in color; and good garden performance.

2 Drawing Sheets

Figure 1:
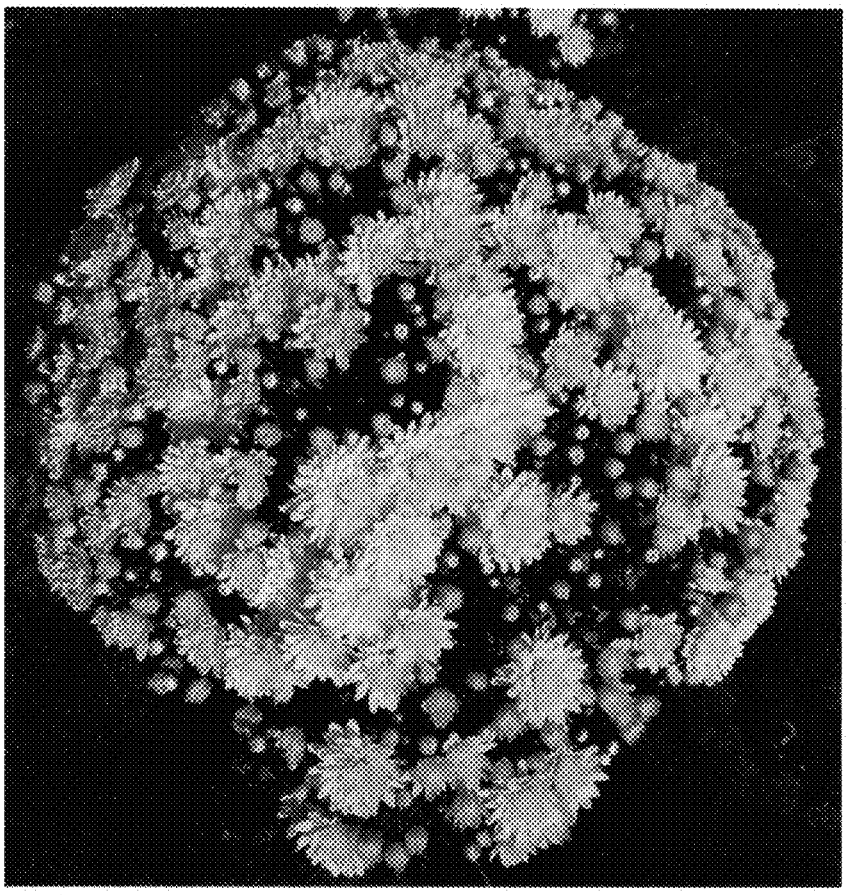

Botanical designation: *Chrysanthemum* X *morifolium*.
Cultivar denomination: 'ZANMUTRIBE YELLOW'.

CROSS-REFERENCED TO CLOSELY-RELATED APPLICATIONS

Title: *Chrysanthemum* Plant Named 'Zanmutribe Dapi'
Inventor/Applicant: Wilhelmus Bernardus Blom
Filed: Mar. 16, 2023 (Co-pending U.S. Plant patent application Ser. No. 18/122,322)
Title: *Chrysanthemum* Plant Named 'Zanmutribe Orange'
Inventor/Applicant: Wilhelmus Bernardus Blom
Filed: Mar. 16, 2023 (Co-pending U.S. Plant patent application Ser. No. 18/122,334)

BACKGROUND OF THE INVENTION

The present invention relates to a new and distinct cultivar of *Chrysanthemum* plant, botanically known as *Chrysanthemum* X *morifolium*, commercially referred to as a Garden Mum and hereinafter referred to by the name 'Zanmutribe Yellow'.

The new *Chrysanthemum* plant is a product of a planned breeding program conducted by the Inventor in Rijsenhout, The Netherlands. The objective of the breeding program is to create new uniform spherically-shaped and early flowering *Chrysanthemum* plants with decorative-type inflorescences and attractive ray floret coloration.

The new *Chrysanthemum* plant is a naturally-occurring whole plant mutation of *Chrysanthemum* x *morifolium* 'Zanmutribe', not patented. The new *Chrysanthemum* plant was discovered and selected as a single flowering plant from within a population of plants of 'Zanmutribe' in a controlled greenhouse environment in Rijsenhout, The Netherlands in September, 2018.

Asexual reproduction of the new *Chrysanthemum* plant by vegetative terminal cuttings was first conducted in a controlled greenhouse environment in Rijsenhout, The Netherlands since October, 2018. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Zanmutribe Yellow'. These characteristics in combination distinguish 'Zanmutribe Yellow' as a new and distinct *Chrysanthemum* plant:

1. Upright, outwardly spreading and uniformly spherical plant habit.
2. Moderately vigorous growth habit and moderate growth rate.
3. Freely branching habit; dense and full plant habit.
4. Early and freely flowering habit.
5. Long flowering period.
6. Decorative-type inflorescences with ray florets that are yellow in color.
7. Good garden performance.

Plants of the new *Chrysanthemum* can be compared to plants of the mutation parent, 'Zanmutribe'. Plants of the new *Chrysanthemum* differ primarily from plants of 'Zanmutribe' in ray floret color as ray florets of plants of the new *Chrysanthemum* are yellow in color whereas ray florets of plants of 'Zanmutribe' are pink in color.

Plants of the new *Chrysanthemum* can be compared to plants of *Chrysanthemum* X *morifolium* 'Zanmutribe Dapi', disclosed in U.S. Plant patent application Ser. No. 18/122,322 filed concurrently. Plants of the new *Chrysanthemum* differ primarily from plants of 'Zanmutribe Dapi' in ray floret color as ray florets of plants of the new *Chrysanthemum* are yellow in color whereas ray florets of plants of 'Zanmutribe Dapi' are dark purplish pink in color.

Plants of the new *Chrysanthemum* can be compared to plants of *Chrysanthemum* X *morifolium* 'Zanmutribe Orange', disclosed in U.S. plant patent application Ser. No. 18/122,334 filed concurrently. Plants of the new *Chrysanthemum* differ primarily from plants of 'Zanmutribe Orange' in ray floret color as ray florets of plants of the new *Chrysanthemum* are yellow in color whereas ray florets of plants of 'Zanmutribe Orange' are orange in color.

Plants of the new *Chrysanthemum* can also be compared to plants of *Chrysanthemum* X *morifolium* 'Zanmumadore Yellow', disclosed in U.S. Plant Pat. No. 31,021. In side-by-side comparisons, plants of the new *Chrysanthemum* differ primarily from plants of 'Zanmumadore Yellow' in response time as plants of the new *Chrysanthemum* flower about four weeks earlier than plants of 'Zanmumadore Yellow'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a top perspective view of a typical flowering plant of 'Zanmutribe Yellow' grown in a container.

Figure 2:
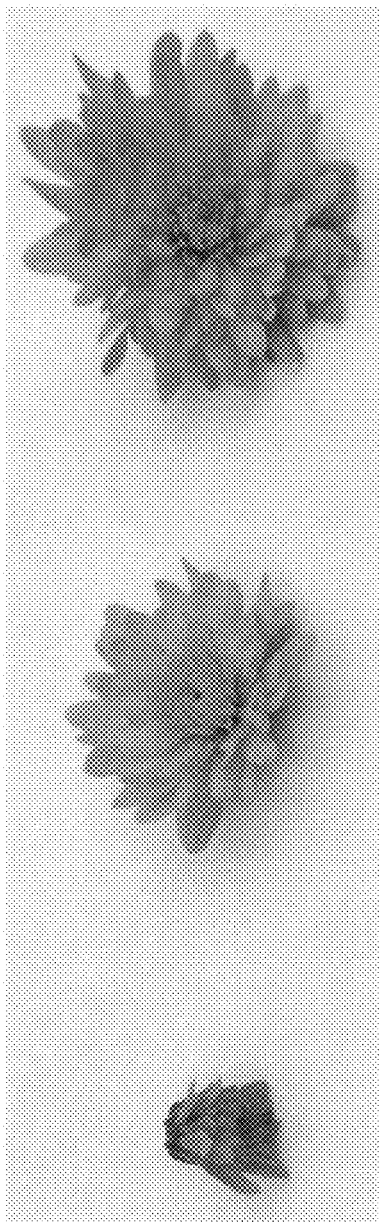

The photograph on the second sheet (FIG. 2) is a close-up view of developing and fully developed inflorescences from typical flowering plants of 'Zanmutribe Yellow'.

DETAILED BOTANICAL DESCRIPTION

The aforementioned photographs and following observations and measurements describe plants grown in 17-cm containers in an outdoor nursery in Rijsenhout, The Netherlands under natural daylengths during the summer and autumn and under cultural practices generally used in commercial *Chrysanthemum* production. During the production of the plants, day temperatures ranged from 15° C. to 25° C. and night temperatures ranged from 8° C. to 15° C. Plants were 16 weeks from planting when the photograph was taken and the detailed description was taken on plants from 13 to 20 weeks after planting. In the following description, color references are made to The Royal Horticultural Society Colour Chart, 2015 Edition, except where general terms of ordinary dictionary significance are used.

Botanical classification: *Chrysanthemum* X Morifolium 'Zanmutribe Yellow'.

Parentage: Naturally-occurring whole plant mutation of *Chrysanthemum* x *morifolium* 'Zanmutribe', not patented.

Propagation:

*Type cutting.*—By vegetative tip cuttings.

*Time to initiate roots, summer.*—About six to eight days at temperatures about 12° C. to 23° C.

*Time to produce a rooted young plant, summer.*—About 12 to 13 days at temperatures about 12° C. to 23° C.

*Root description.*—Thin, fibrous; typically close to 164D in color; actual color of the roots is dependent on substrate composition, water quality, fertilizer type and formulation, substrate temperature and physiological age of roots.

*Rooting habit.*—Freely branching; dense.

Plant description:

*Appearance.*—Perennial decorative-type *Chrysanthemum*; stems upright and outwardly spreading giving a uniformly rounded appearance to the plant; plants spherical in overall shape; very freely branching habit, about six to seven primary lateral branches develop, each primary lateral branch with about eight to nine secondary branches; dense, bushy and full plant habit; moderately vigorous growth habit and moderate growth rate.

*Plant height.*—About 28 cm to 30 cm.

*Plant width.*—About 40 cm.

*Lateral branches.*—Length: About 14 cm to 17 cm. Diameter: About 1.5 mm. Internode length: About 1 cm to 1.5 cm. Strength: Moderately strong. Aspect: About 30 to 45 degrees from vertical. Texture and luster: Pubescent; longitudinally ridged; matte. Color: Close to 138B; with development, towards the base becoming closer to 199D.

*Leaves.*—Arrangement: Alternate, simple. Length: About 2 cm to 7 cm. Width: About 1.1 cm to 4.5 cm. Shape: Broadly elliptic. Apex: Acute, pointed. Base: Attenuate. Margin: Palmately lobed, sinuses between lateral lobes divergent and medium in depth. Texture and luster, upper surface: Pubescent; slightly glossy. Texture and luster, lower surface: Pubescent; matte. Venation: Palmate and pinnate. Color: Developing and fully expanded leaves, upper surface: Close to 139A; venation, close to 147D. Developing and fully expanded leaves, lower surface: Close to NN137B; venation, close to 148D. Petioles: Length: About 3 mm to 11 mm. Diameter: About 1.5 mm to 2.1 mm. Strength: Moderately strong. Texture and luster, upper and lower surfaces. Pubescent; slightly glossy. Color, upper surface: Close to 147D. Color, lower surface: Close to 148D.

Inflorescence description:

*Appearance.*—Decorative-type inflorescence form; inflorescences borne on terminals above foliar plane; ray florets arranged acropetally on a capitulum; inflorescences facing upright to outwardly.

*Fragrance.*—Faintly fragrant, pungent and aromatic.

*Flowering response.*—Early flowering habit and long flowering period; under natural season conditions, plants flower from week 37 to week 42 in The Netherlands.

*Postproduction longevity.*—Inflorescences maintain good color and substance for about three weeks in an outdoor nursery; inflorescences persistent.

*Quantity of inflorescences.*—Freely flowering habit; about 340 to 350 inflorescences develop per plant.

*Inflorescence buds.*—Height: About 4 mm. Diameter: About 7 mm. Shape: Rounded. Texture and luster: Pubescent; matte. Color: Close to 139C.

*Inflorescence diameter.*—About 6 cm.

*Inflorescence depth (height).*—About 1.8 cm.

*Disc diameter.*—To date, disc development has not been observed on plants of the new *Chrysanthemum*.

*Receptacle diameter.*—About 4 mm.

*Receptacle height.*—About 2 mm to 3 mm.

*Receptacle shape.*—Domed.

*Receptacle color.*—Close to 144B.

*Ray florets.*—Number of ray florets per inflorescence: About 140 to 160 ray florets arranged in about twelve whorls. Length: About 1 cm to 2.8 cm. Width:

About 1.5 cm to 4 cm. Shape: Elliptic. Apex: Acute, pointed to emarginate. Base: Attenuate. Margin: Entire; not undulate. Aspect: Mostly flat. Texture and luster, upper and lower surfaces: Smooth, glabrous; slightly glossy. Color: When opening, upper surface: Close to 12A. When opening, lower surface: Close to 12B. Fully opened, upper surface: Close to 8A; venation, close to 8A; color does not change with subsequent development. Fully opened, lower surface: Close to 8C; venation, close to 8C; color does not change with subsequent development.

*Phyllaries.*—Number of phyllaries per inflorescence: About 24 phyllaries arranged in about three whorls. Length: About 5 mm to 6 mm. Width: About 1.5 mm. Shape: Elliptic. Apex: Acute, pointed. Base: Attenuate. Margin: Entire. Texture and luster, upper and lower surfaces: Pubescent; matte. Color, upper surface: Close to 139C. Color, lower surface: Close to 138B to 138C.

*Peduncles.*—Length, terminal peduncle: About 5 cm. Length, third peduncle: About 7.5 cm. Diameter, terminal peduncle: About 1 mm. Diameter, third peduncle: About 1 mm. Strength: Moderately strong. Aspect, terminal peduncle: Mostly upright. Aspect, third peduncle: About 30 degrees from lateral branch axis. Texture and luster: Pubescent; matte. Color: Close to 138C.

*Reproductive organs.*—Androecium: Not observed. Gynoecium: Number of pistils per ray floret: One. Pistil length: About 3 mm. Style length: About 2.5 mm. Style color: Close to 149C. Stigma diameter: About 1 mm. Stigma shape: Forked. Stigma color: Close to 12A. Ovary color: Close to 149C.

*Seeds and fruits.*—To date, seed and fruit production have not been observed on plants of the new *Chrysanthemum.*

Garden performance: Plants of the new *Chrysanthemum* have demonstrated good garden performance and will tolerate temperatures ranging from about 4° C. to about 30° C.

It is claimed:

1. A new and distinct *Chrysanthemum* plant named 'Zanmutribe Yellow' as illustrated and described.

* * * * *